(12) United States Patent
Sugahara (10) Patent No.: US 11,205,269 B2
(45) Date of Patent: Dec. 21, 2021

(54) LEARNING DATA CREATION SUPPORT APPARATUS, LEARNING DATA CREATION SUPPORT METHOD, AND LEARNING DATA CREATION SUPPORT PROGRAM

(71) Applicant: FUJIFILM Corporation, Tokyo (JP)

(72) Inventor: Masataka Sugahara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 16/277,360

(22) Filed: Feb. 15, 2019

(65) Prior Publication Data

US 2019/0272640 A1 Sep. 5, 2019

(30) Foreign Application Priority Data

Mar. 2, 2018 (JP) .............................. JP2018-037977

(51) Int. Cl.
*G06T 7/00* (2017.01)
*G06K 9/62* (2006.01)
*G16H 30/40* (2018.01)
*G06N 20/00* (2019.01)

(52) U.S. Cl.
CPC .......... *G06T 7/0016* (2013.01); *G06K 9/6262* (2013.01); *G06N 20/00* (2019.01); *G16H 30/40* (2018.01); *G06T 2207/20081* (2013.01); *G06T 2207/30068* (2013.01); *G06T 2207/30096* (2013.01)

(58) Field of Classification Search
CPC ......... G06T 7/0016; G06T 2207/20081; G06T 2207/30068; G06T 2207/30096; G16H 30/40; G06N 20/00; G06K 9/6262

USPC .......................................................... 382/128
See application file for complete search history.

(56) References Cited

U.S. PATENT DOCUMENTS 5,715,182 A * 2/1998 Asai ....................... G01N 15/14
702/22
2009/0268952 A1 10/2009 Schaffer et al.
2017/0032090 A1* 2/2017 Kamen .................. G16H 10/60

FOREIGN PATENT DOCUMENTS

| CN | 107688815 A | 2/2018 |
| JP | 2007-279942 A | 10/2007 |
| JP | 2008-523876 A | 7/2008 |
| JP | 2010-252989 A | 11/2010 |

(Continued)

OTHER PUBLICATIONS

Japanese Office Action, dated Nov. 4, 2020, for corresponding Japanese Application No. 2018-037977, with an English translation.

*Primary Examiner* — Wednel Cadeau
(74) *Attorney, Agent, or Firm* — Birch, Stewart, Kolasch & Birch, LLP (57) ABSTRACT

Provided are a learning data creation support apparatus, a learning data creation support method, and a learning data creation support program that create learning data required for learning without performing a complicated operation. Image-before-biopsy acquisition means acquires, as an image before biopsy, an image of a biopsy target part of a patient captured at a date and time within a predetermined range before an examination date and time of the biopsy. In a case in which a biopsy result indicated by biopsy data indicates a lesion, registration means registers a lesion candidate obtained by performing an image analysis process for the image before biopsy as correct answer data.

12 Claims, 8 Drawing Sheets

(56) References Cited

FOREIGN PATENT DOCUMENTS

| JP | 2010252989 A | * | 11/2010 |
| JP | 2019-526869 A | | 9/2019 |
| WO | WO 2018/031919 A1 | | 2/2018 |

* cited by examiner

LEARNING DATA CREATION SUPPORT APPARATUS, LEARNING DATA CREATION SUPPORT METHOD, AND LEARNING DATA CREATION SUPPORT PROGRAM

CROSS REFERENCE TO RELATED APPLICATIONS

This application claims priority under 35 U.S.C. § 119(a) to Patent Application No. 2018-037977 filed in Japan on Mar. 2, 2018, all of which are hereby expressly incorporated by reference into the present application.

BACKGROUND OF THE INVENTION

1. Field of the Invention

The present invention relates to a learning data creation support apparatus, a learning data creation support method, and a learning data creation support program.

2. Description of the Related Art

In recent years, machine learning has been used in order to learn the characteristics of data and to recognize and classify, for example, images. In recent years, various learning methods have been developed and the processing time has been reduced with the improvement of the processing capability of computers. Therefore, it is possible to perform deep learning in which a system learns the characteristics of, for example, image data at a deeper level. The performance of deep learning makes it possible to recognize the characteristics of, for example, images with very high accuracy. The discrimination performance is expected to be improved.

In a medical field, artificial intelligence (AI) which performs learning using a deep learning method to recognize the characteristics of an image with high accuracy is preferable. In the deep learning, it is necessary to perform learning with a large amount of high-quality data suitable for the purpose. Therefore, it is important to efficiently prepare learning data. In each medical institution, image data for many cases is accumulated with the spread of a picture archiving and communication system (PACS). Therefore, a technique has been examined which performs learning using image data for various cases accumulated in each medical institution.

In addition, in the medical field, whether an image is a correct answer or an incorrect answer is learned using an image of a shadow, such as a tumor appearing on an image, as learning data to discriminate the shadow appearing on the image. For example, JP2008-523876A discloses a method in which the actual image of a patient having different types of lesions is interpreted by a plurality of experts, such as radiologists, and learning data is created on the basis of a plurality of types of images and the interpretation result of the images by a plurality of reliable and skilled radiologists to improve the reliability of the learning data.

SUMMARY OF THE INVENTION

However, in this method, it takes a lot of time and effort for a person to find the image to be registered as learning data while checking a plurality of images and it is difficult to register a large amount of learning data.

In contrast, in a normal medical examination, in a case in which a disease is suspected, the radiologist interprets an image, such as a CT image or an MRI image, of the part corresponding to the suspected disease. In a case in which there is a suspicious finding, the pathologist performs a thorough examination on the part and makes a definite diagnosis. In a case in which there is a thorough examination result (for example, a pathological result) of a suspicious part found in the image, an abnormal shadow region obtained by an image analysis process can be confirmed as correct answer data.

In order to solve the above-mentioned problems, an object of the invention is to provide a learning data creation support apparatus, a learning data creation support method, and a non-transitory computer readable recording medium storing a learning data creation support program that can create learning data required for learning without performing a complicated operation.

According to an aspect of the invention, there is provided a learning data creation support apparatus comprising: biopsy data acquisition means for acquiring biopsy data indicating a result of a biopsy performed for a patient; image-before-biopsy acquisition means for acquiring, as an image before biopsy, an image of a biopsy target part of the patient captured at a date and time within a predetermined range before an examination date and time of the biopsy; and registration means for, in a case in which the biopsy result indicated by the biopsy data indicates a lesion, registering, as correct answer data, an image of a lesion candidate region obtained by performing an image analysis process for the image before biopsy or the image before biopsy.

According to another aspect of the invention, there is provided a learning data creation support method performed in a learning data creation support apparatus. The learning data creation support method comprises: a biopsy data acquisition step of acquiring biopsy data indicating a result of a biopsy performed for a patient; an image-before-biopsy acquisition step of acquiring, as an image before biopsy, an image of a biopsy target part of the patient captured at a date and time within a predetermined range before an examination date and time of the biopsy; and a registration step of, in a case in which the biopsy result indicated by the biopsy data indicates a lesion, registering, as correct answer data, an image of a lesion candidate region obtained by performing an image analysis process for the image before biopsy or the image before biopsy.

According to still another aspect of the invention, there is provided a non-transitory computer recording medium storing a learning data creation support program that causes a computer to perform: a biopsy data acquisition step of acquiring biopsy data indicating a result of a biopsy performed for a patient; an image-before-biopsy acquisition step of acquiring, as an image before biopsy, an image of a biopsy target part of the patient captured at a date and time within a predetermined range before an examination date and time of the biopsy; and a registration step of, in a case in which the biopsy result indicated by the biopsy data indicates a lesion, registering, as correct answer data, an image of a lesion candidate region obtained by performing an image analysis process for the image before biopsy or the image before biopsy.

The "lesion candidate region" means a region that is likely to be a lesion on the image and indicates a region that is more likely to be a lesion extracted by the image analysis process of the computer than other regions in the image.

The "correct answer data" means data in which a correct answer label is attached to the lesion candidate region. In a case in which the lesion candidate region is determined to be an image of a lesion, the lesion candidate region is correct answer data. Alternatively, the "correct answer data" means data in which a correct answer label is attached to an image before biopsy. In a case in which the image before biopsy is determined to be an image indicating a lesion, the image before biopsy is correct answer data.

Preferably, in a case in which the image of the lesion candidate region is registered, the registration means specifies a correspondence position corresponding to a position where the biopsy has been performed in the image before biopsy from two partial images of the target part captured in different directions. Preferably, in a case in which the biopsy result indicates a lesion, the registration means registers, as the correct answer data, an image of a lesion candidate region at a position matched with the correspondence position among positions of a plurality of lesion candidate regions obtained from the image before biopsy.

For the "matching between the position of the lesion candidate region and the correspondence position", in a case in which the positions are within a predetermined reference range, the positions may be determined to be matched with each other. In addition, the positions may be within a range that is appropriately determined according to the performance of the computer and the resolution of the image.

Preferably, the learning data creation support apparatus may further comprise learning means for, in a case in which the image of the lesion candidate region is registered, detecting a lesion candidate region, using a discriminator that has learned the correct answer data of the image of the lesion candidate region, and directing the discriminator to relearn the correct answer data of the registered image of the lesion candidate region.

The learning data creation support apparatus may further comprise: learning means for, in a case in which the image before biopsy is registered, detecting whether an image indicating a lesion is present, using a discriminator that has learned the correct answer data of the image before biopsy, and directing the discriminator to relearn the correct answer data of the registered image before biopsy.

The image of the biopsy target part may be a mammographic image.

According to yet another aspect of the invention, there is provided a learning data creation support apparatus comprising: a memory that stores commands for causing a computer to perform processes; and a processor that is configured to execute the stored commands. The processor acquires biopsy data indicating a result of a biopsy performed for a patient, acquires, as an image before biopsy, an image of a biopsy target part of the patient captured at a date and time within a predetermined range before an examination date and time of the biopsy, and registers, as correct answer data, a lesion candidate region obtained by performing an image analysis process for the image before biopsy in a case in which the biopsy result indicated by the biopsy data indicates a lesion.

According to the invention, it is possible to create learning data required for learning, without performing a complicated operation.

DESCRIPTION OF THE PREFERRED EMBODIMENTS

Figure 1:
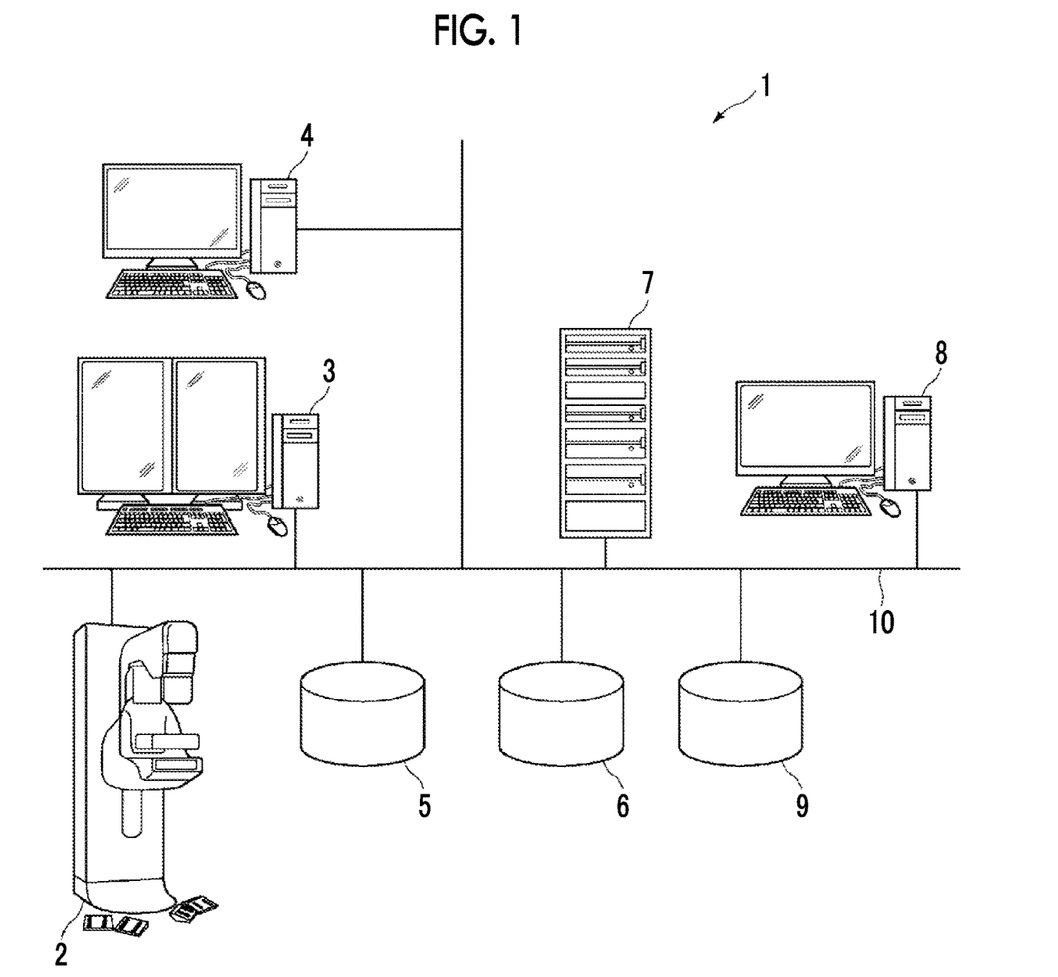
FIG. 1 is a diagram illustrating an example of the schematic configuration of a medical information system.

Hereinafter, a first embodiment of the invention will be described with reference to the drawings. FIG. 1 illustrates the schematic configuration of a medical information system 1 provided with a learning data creation support apparatus according to the first embodiment of the invention.

The medical information system 1 is used to capture an image of an examination target part of a subject and to store the image on the basis of an examination order from a doctor in a diagnosis and treatment department, is used by a radiologist in a radiology department to interpret the captured image and to make an interpretation report, is used for a pathology examination, such as a biopsy, and is used to make a pathology report. As illustrated in FIG. 1, the medical information system 1 is configured by connecting a modality 2, a radiologist workstation 3, a diagnosis and treatment department workstation 4, an image database 5, an interpretation report database 6, an image processing server 7, a pathology examination workstation 8, and a pathology report database 9 so as to communicate with each other through a network 10. An application program that causes each apparatus to function as a component of the medical information system 1 is installed in each apparatus. In addition, the application program may be installed from a recording medium, such a CD-ROM, or may be downloaded from a storage device of a server connected through a network, such as the Internet, and then installed.

The modality 2 includes an apparatus that captures an image of an examination target part of the subject, generates an examination image indicating the part, adds accessory information defined by a digital imaging and communication in medicine (DICOM) standard to the image, and outputs the image. Examples of the modality include a mammography apparatus, a computed tomography (CT) apparatus, a magnetic resonance imaging (MM) apparatus, a positron emission tomography (PET) apparatus, an ultrasound apparatus, and a computed radiography (CR) apparatus using a flat panel detector (FPD).

The radiologist workstation 3 (hereinafter, the radiologist workstation is referred to as a radiologist WS 3) is a computer that is used by a radiologist in the radiology department to interpret an image and to make an interpretation report. The radiologist WS 3 comprises known hardware configurations, such as a central processing unit (CPU), a main storage device, an auxiliary storage device, an input/output interface, a communication interface, an input device, a display device, and a data bus. For example, a known operation system is installed in the radiologist WS 3. The radiologist WS 3 includes one high-definition display or a plurality of high-definition displays as the display device. In the radiologist WS 3, processes, such as the display of an image received from the image database 5, the display of the detection result of a portion that appears to be a lesion in an image by an image processing server, and the making of an interpretation report, are performed by executing software programs for each process. In addition, in the radiologist WS 3, the input device including, for example, a keyboard and a mouse, is used to input an interpretation report on an interpretation target. In a case in which the input of the interpretation report is completed, the radiologist WS 3 requests the registration of the interpretation report to the interpretation report database 6 through the network 10.

For example, the diagnosis and treatment department workstation 4 (hereinafter, the diagnosis and treatment department workstation is referred to as a diagnosis and treatment department WS 4) is a computer that is used by a doctor in the diagnosis and treatment department to observe an image in detail, to read an interpretation report, to read an electronic chart, and to input an electronic chart. The diagnosis and treatment department WS 4 comprises known hardware configurations, such as a CPU, a main storage device, an auxiliary storage device, an input/output interface, a communication interface, an input device, a display device, and a data bus. For example, a known operation system is installed in the diagnosis and treatment department WS 4 and the diagnosis and treatment department WS 4 includes one display or a plurality of displays as the display device. In the diagnosis and treatment department WS 4, processes, such as the display of an image received from the image database 5, the automatic detection or highlight display of a portion that appears to be a lesion in the image, and the display of an interpretation report received from the interpretation report database 6, are performed by executing software programs for each process.

A software program that provides the functions of a database management system (DBMS) to a general-purpose computer is incorporated into the image database 5 and the image database 5 comprises a storage. The storage may be a hard disk drive, a network attached storage (NAS) connected to the network 10, or a disk device connected to a storage area network (SAN). In addition, image data captured by the modality 2 is transmitted to the image database 5 through the network 10 according to a storage format and a communication standard based on the DICOM standard and is then stored in the image database 5. The examination images of a plurality of patients captured by the modality 2 and accessory information are registered in the image database 5. For example, an image identification (ID) for identifying an individual image, a patient ID for identifying a subject, the examination date and time when the examination image was generated, the type of modality used in the examination for acquiring the examination image, patient information including the name, age, and sex of the patient, and an examination part (imaging part) are recorded on the accessory information.

A software program that provides the functions of a database management system (DBMS) to a general-purpose computer is incorporated into the interpretation report database 6 and the interpretation report database 6 comprises a high-capacity storage. The storage may be a high-capacity hard disk drive, a NAS connected to the network 10, or a disk device connected to a SAN. For example, an interpretation report on which information including an image ID for identifying an interpretation target image, a radiologist ID for identifying the radiologist who has interpreted images, a lesion name, a lesion region, the positional information of a lesion, and the doctor's opinion has been recorded is registered in the interpretation report database 6.

The image processing server 7 is a computer that is used to perform various image analysis processes for the image captured by the modality 2 and comprises known hardware configurations, such as a CPU, a main storage device, an auxiliary storage device, an input/output interface, a communication interface, an input device, a display device, and a data bus. For example, a known operation system is installed in the image processing server 7. In addition, for example, the image processing server 7 performs the image analysis process to detect a region that appears to be a lesion in the image in response to a request from the radiologist WS 3 or the diagnosis and treatment department WS 4.

The pathology examination workstation 8 (Hereinafter, the pathology examination workstation is referred to as a pathology examination WS 8) is a computer that is used by a pathologist to read a pathology report based on a biopsy result and to read and input a pathology report. The pathology examination WS 8 comprises known hardware configurations, such as a CPU, a main storage device, an auxiliary storage device, an input/output interface, a communication interface, an input device, a display device, and a data bus. For example, a known operation system is installed in the pathology examination WS 8. The pathology examination WS 8 includes a display as the display device. The pathology examination WS 8 executes a software program for each process, such as the making of a pathology report, to perform each process. In a case in which the input of the pathology report is completed, the pathology examination WS 8 requests the registration of the pathology report to the pathology report database 9 through the network 10.

A software program that provides the functions of a database management system (DBMS) to a general-purpose computer is incorporated into the pathology report database 9 and the pathology report database 9 comprises a high-capacity storage. The storage may be a high-capacity hard disk drive, a NAS connected to the network 10, or a disk device connected to a SAN. For example, a pathology report on which information including a patient ID, a pathologist ID for identifying a pathologist, a lesion name, the positional information of a lesion, and the doctor's opinion has been recorded is registered in the pathology report database 9.

The network 10 is a local area network that connects various apparatuses in the hospital. In a case in which the radiologist WS 3 or the pathology examination WS 8 is installed in another hospital or a medical office, the network 10 may be configured by connecting the local area networks of each hospital with the Internet or a leased line. In any case, an optical network is given as an example of the network 10.

Hereinafter, in this embodiment, a specific example in which a biopsy position is specified from a mammographic image of the breast of a patient and then a biopsy is performed will be described. In this embodiment, the modality 2 is described as a mammography apparatus 2. Here, the mammography apparatus 2 according to this embodiment will be described in detail with reference to FIGS. 2 to 5.

Figure 2:
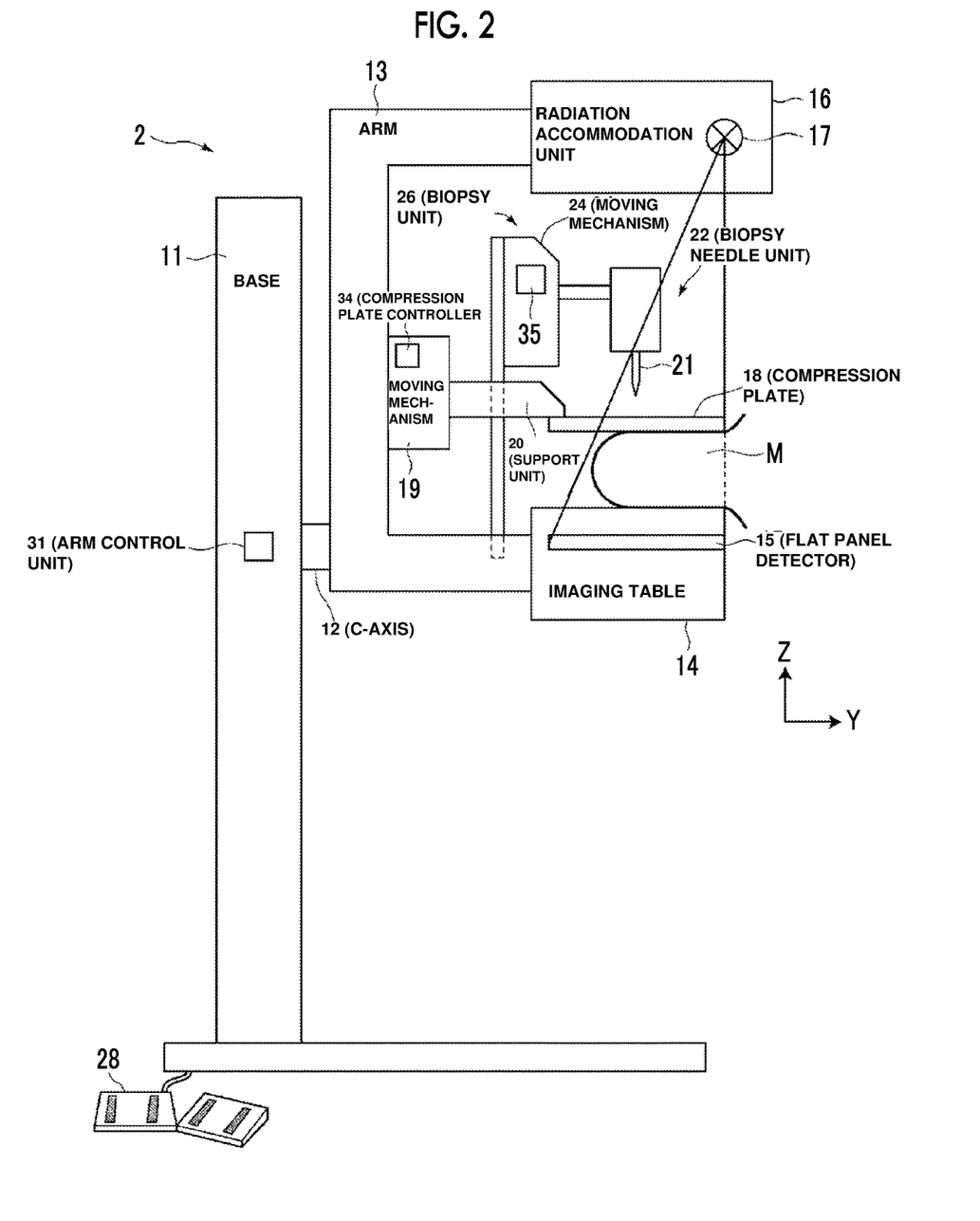
FIG. 2 is a diagram schematically illustrating an example of the configuration of a mammography apparatus according to this embodiment.

For example, as illustrated in FIG. 2, in the mammography apparatus 2, a radiation accommodation unit 16 that accommodates a radiation emitting unit 17 and an imaging table 14 are connected to an arm 13 so as to face each other. An image recording medium, such as a flat panel detector 15, is set in the imaging table 14 while being accommodated in a recording medium holding unit, such as a cassette. The arm 13 is attached to a base 11 by a C-axis 12. In addition, the C-axis 12 having a rotation center at the center position of the flat panel detector 15 is attached such that the rotation center of the arm 13 is the center of the flat panel detector 15 in the X-axis direction (see FIG. 3) and the arm 13 is provided in the base 11.

The base 11 is provided with an operation unit 28 that is used by an operator to adjust the height of the imaging table 14 (that is, the height of the arm 13) and the inclination of the imaging table 14 (that is, the inclination of the arm 13) and an arm control unit 31 that moves the arm 13 in the vertical direction and rotates the arm 13 in response to an input from the operation unit 28.

The arm control unit 31 rotates the C-axis 12 attached to the base 11 to adjust the inclination of the arm 13 and moves the arm 13 in the vertical direction to adjust the height of the imaging table 14.

A compression plate 18 that is provided above the imaging table 14 and compresses the breast, a support unit 20 that supports the compression plate 18, and a moving mechanism 19 that moves the support unit 20 along the arm 13 in the vertical direction are provided in a central portion of the arm 13. The position and compression force of the compression plate 18 are controlled by a compression plate controller 34.

Figure 3:
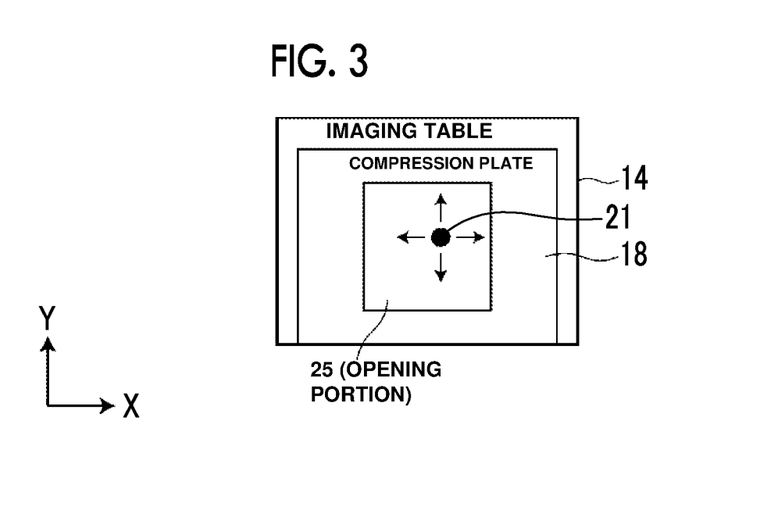
FIG. 3 is a plan view schematically illustrating a compression plate as viewed from the upper side.

FIG. 3 is a top view illustrating the compression plate 18. As illustrated in FIG. 3, the compression plate 18 comprises an opening portion 25 having a square shape with a size of about 10 cm×10 cm such that a biopsy is performed with the breast fixed by the imaging table 14 and the compression plate 18.

For example, a biopsy unit 26 illustrated in FIG. 2 comprises a biopsy needle 21 that is inserted into the breast, a biopsy needle unit 22, and a moving mechanism 24 that moves the biopsy needle unit 22 in the X, Y and Z directions. The position of the tip of the biopsy needle 21 of the biopsy needle unit 22 is controlled by a needle position controller 35 provided in the moving mechanism 24. In FIG. 3, the horizontal direction is the X direction, the vertical direction is the Y direction, and a direction perpendicular to the XY plane is the Z direction.

Figure 4:
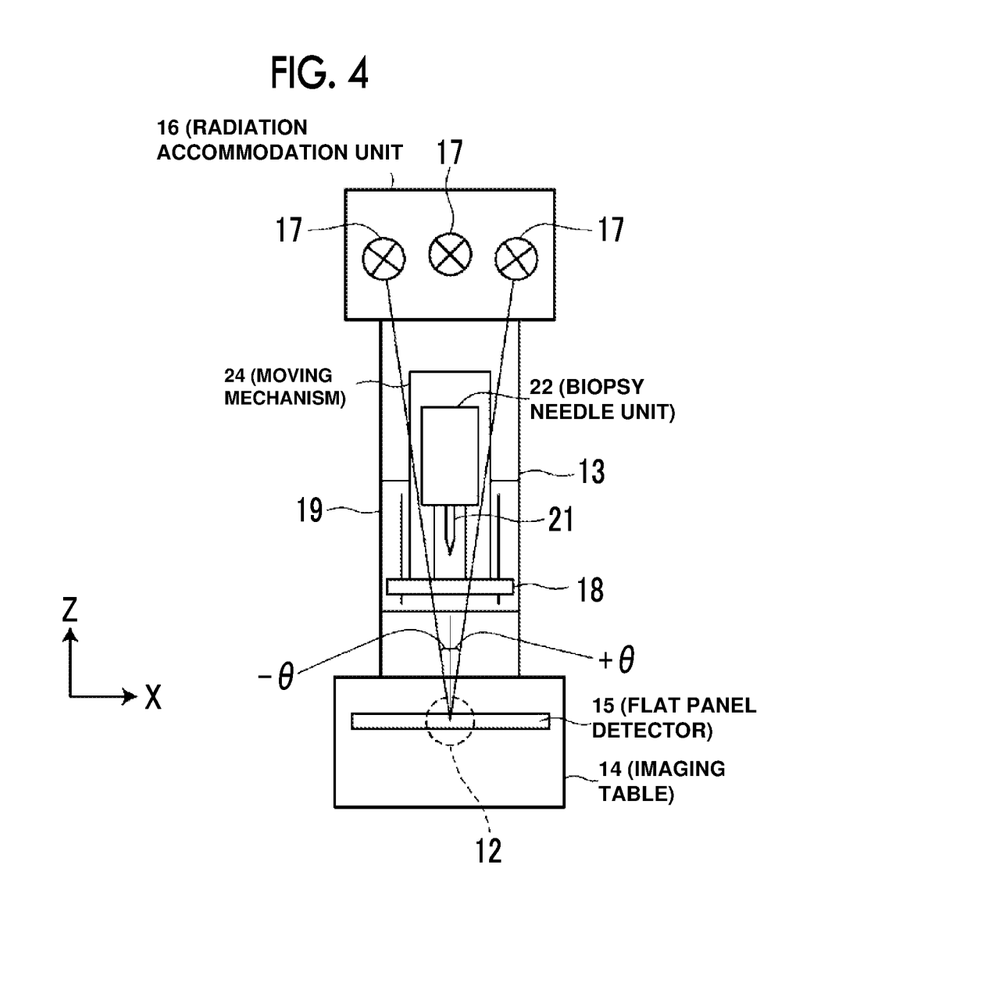
FIG. 4 is a diagram illustrating an example of an aspect in which a radiation emitting unit is inclined to the left and right sides in a direction along an arm.

The mammography apparatus 2 acquires scout images captured in two directions so as to include a target region of the breast to be biopsied before needling. The scout images are images that are viewed from different view points in order to check a pathology examination position. For example, as illustrated in FIG. 4, two partial images captured in the directions (which are inclined by, for example, 15° in each of the +θ and −θ directions illustrated in FIG. 4) in which the radiation emitting unit 17 is inclined from a direction along the arm 13 to the left and right sides are referred to as the scout images. In addition, the scout images are stored in the image database 5 through the network 10.

Figure 5:
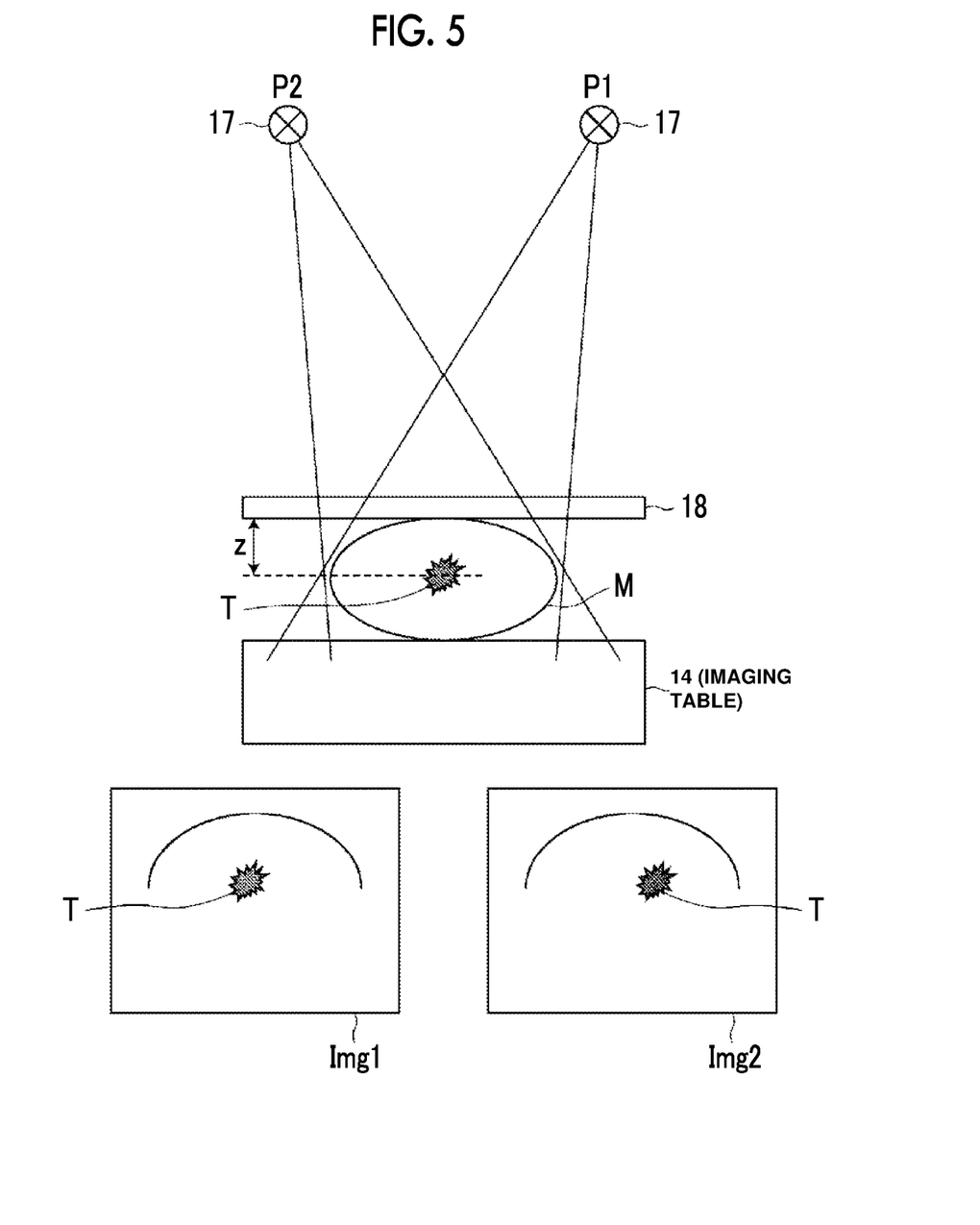
FIG. 5 is a diagram illustrating an example of the relationship between the position of the radiation emitting unit and two scout images.

FIG. 5 is a diagram illustrating an example of the relationship between the position of the radiation emitting unit 17 and two scout images. In a scout image Img1 captured with the radiation emitting unit 17 located at a position P1, the position of a target T leans to the left. In a scout image Img2 captured with the radiation emitting unit 17 located at a position P2, the position of the target T leans to the right. A distance z from the bottom (the side to which the breast is pressed) of the compression plate 18 to the target T and the position of the target T in the XY plane can be calculated from the positional deviation of the target T between two scout images Img1 and Img2 and the three-dimensional positional information of the target T can be obtained.

In a case in which the positional information of the target T is received, the needle position controller 35 of the biopsy unit 26 moves the tip of the biopsy needle 21 to the position of the target T and inserts the biopsy needle 21 into the breast.

Figure 6:
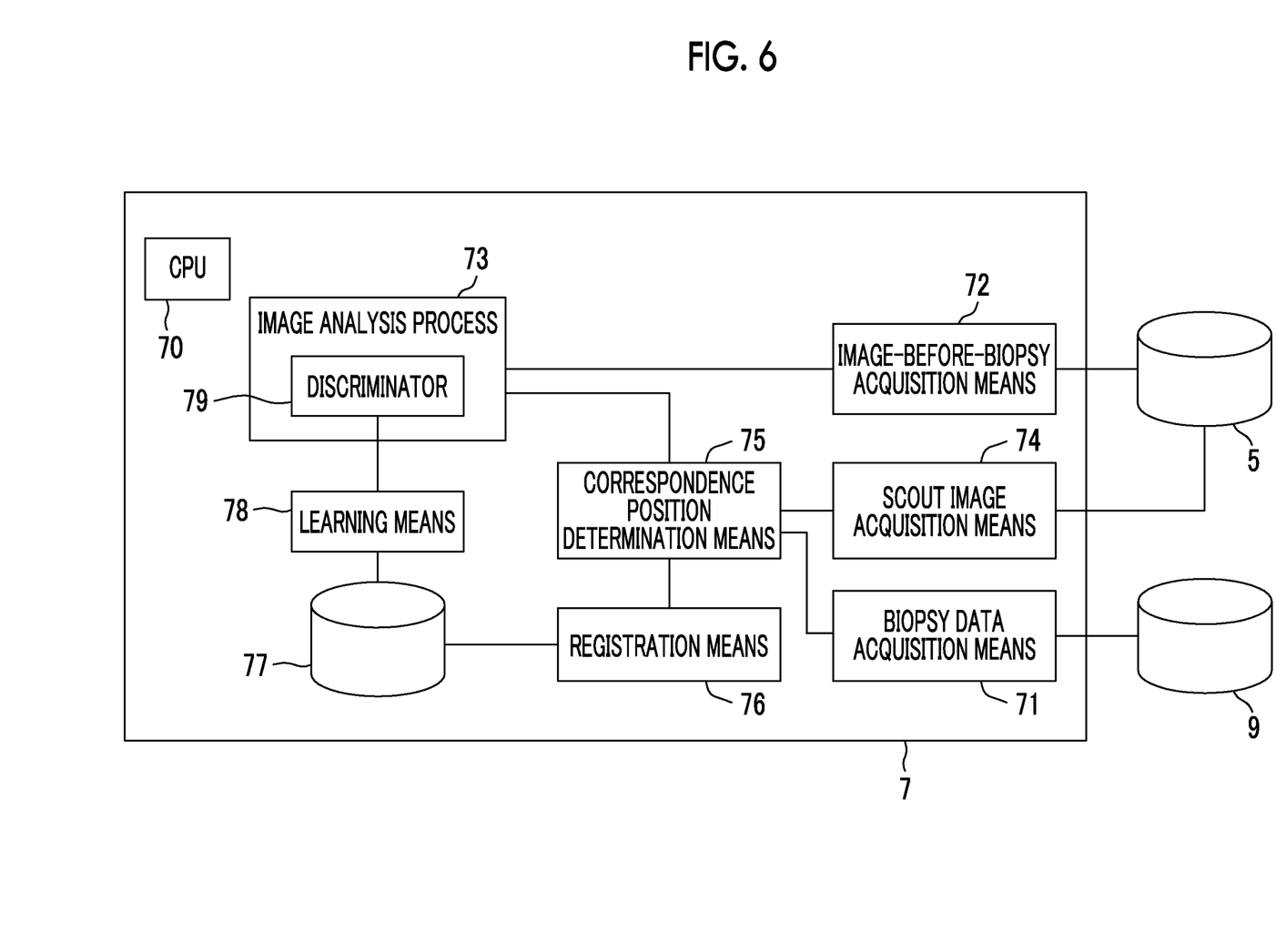
FIG. 6 is a diagram illustrating an example of the schematic configuration of a learning data creation support apparatus.

Next, the learning data creation support apparatus according to this embodiment will be described with reference to FIG. 6. In this embodiment, a learning data creation support program is installed in the image processing server 7 such that the image processing server 7 functions as the learning data creation support apparatus according to the invention. The learning data creation support program may be stored in a storage device of a computer connected to the network or a network storage so as to be accessed from the outside, may be downloaded to the image processing server 7, and then may be installed in the image processing server 7. Alternatively, the learning data creation support program may be recorded on a recording medium, such as a digital versatile disc (DVD) or a compact disc read only memory (CD-ROM), may be distributed, and may be installed in a computer from the recording medium.

In a case in which the image processing server 7 starts up, the learning data creation support program is stored in a main storage device (not illustrated) and a CPU 70 performs the processes according to the program stored in the main storage device. Hereinafter, the image processing server 7 will be described as a learning data creation support apparatus 7.

Next, the functions of the learning data creation support apparatus 7 will be described. For example, as illustrated in FIG. 6, the learning data creation support apparatus 7 functions as biopsy data acquisition means 71, image-before-biopsy acquisition means 72, image analysis means 73 (hereinafter, referred to as an image analysis process 73), scout image acquisition means 74, correspondence position determination means 75, registration means 76, a learning data storage unit 77, and learning means 78.

The biopsy data acquisition means 71 acquires biopsy data indicating the examination result of the tissues collected by a needling operation of the mammography apparatus 2 from the pathology report database 9. Information including a patient ID, an examination date and time, a target part (for example, the breast), and the position of a target (information of, for example, an inner upper part, an inner lower part, an outer upper part, and an outer lower part of the breast in addition to the right breast or the left breast) is given to the acquired biopsy data.

The image-before-biopsy acquisition means 72 acquires, as an image before biopsy, an image of a biopsy target part of a patient captured at the date and time within a predetermined range before the biopsy examination date and time. For example, since a mammography examination is recommended to be performed every year, a plurality of mammographic images of one patient are stored in the image database 5. The biopsy is performed in a case in which the image analysis process 73 is performed for a captured mammographic image and a shadow (hereinafter, referred to as a lesion candidate) determined to be abnormal is detected. The mammographic image used as a criterion for determining whether to perform a biopsy is the latest image before the biopsy date and time. However, it is considered that an image having a large time difference from the biopsy date and time, for example, an image captured one year or more ago is not the image used as the criterion for determining the biopsy. Therefore, for example, the image-before-biopsy acquisition means 72 searches for the image of the biopsy target part captured within a predetermined range (for example, within two months) before the biopsy date and time among the images a biopsy target part (in this embodiment, the breast) matched with the patient ID of the biopsy data from the image database 5. The searched image is considered to be the mammographic image used as the criterion for determining whether to perform a biopsy immediately before an examination.

The image analysis process 73 is provided with a discriminator 79, discriminates a shadow that appears in the mammographic image using the discriminator 79, detects lesion candidate regions, such as a tumor and calcification, and acquires positional information related to the positions of the lesion candidate regions. The positional information may be a coordinate value in the image, information in which an anatomical position is known, or information of an upper part, a middle part, or a lower part of each organ. For example, in the case of the breast, the positional information may be information of an inner upper part, an inner lower part, an outer upper part, and an outer lower part of each of the left and right breasts. Hereinafter, the discriminator 79 that detects the lesion candidate region is referred to as a first discriminator.

Alternatively, the image analysis process 73 may detect whether the mammographic image is an image in which a lesion is present with the discriminator 79. Hereinafter, the discriminator 79 that detects whether the mammographic image is an image in which a lesion is present is referred to as a second discriminator. For example, in a case in which the image is a mammographic image, a discriminator that can detect whether a lesion is present in each of the CC images of the left and right breasts and the MLO images of the left and right breasts is prepared.

The scout image acquisition means 74 searches for a scout image having an examination date matched with the patient ID of the biopsy data from the image database 5. The mammography apparatus 2 acquires, as the scout images, the partial images of a portion of the breast captured in different directions in a region in which abnormality is recognized in a target part immediately before a biopsy. That is, the scout images are two partial images of a portion of the breast captured on the same date as the examination date.

In a case in which a plurality of lesion candidate regions are detected from the mammographic image by the image analysis process 73, the correspondence position determination means 75 searches for a lesion candidate region having a shadow matched with the shadow appearing in the scout images from the plurality of lesion candidate regions and determines a lesion candidate region at a correspondence position corresponding to the shadow included in the scout images. For the lesion candidate region of the mammographic image matched with the shadow appearing in the scout images, the correspondence position determination means 75 can determine a correspondence position corresponding to the position where a biopsy has been performed from a plurality of lesion candidate regions by finding a lesion candidate region of the mammographic image which has a feature amount most matched with a feature amount extracted from the scout image. An example of the feature amount is a feature amount used to search for a similar image, such as a histogram, scale-invariant feature transform (SIFT), or speeded-up robust features (SURF).

In a case in which the biopsy result indicated by the biopsy data indicates a lesion, the registration means 76 registers, as correct answer data, the lesion candidate region obtained by performing the image analysis process for the image before biopsy. In a case in which one lesion candidate region is obtained by performing the image analysis process for the mammographic image and the biopsy result indicates a lesion, the registration means 76 registers the lesion candidate region as the correct answer data. In contrast, in a case in which a plurality of lesion candidate regions are present, the correspondence position determination means 75 specifies a correspondence position corresponding to the position where a biopsy has been performed in the mammographic image from two scout images and registers, as the correct answer data, a lesion candidate region matched with the correspondence position among the plurality of lesion candidate regions.

Alternatively, in a case in which the biopsy result indicates a lesion, the registration means 76 may register the image before biopsy as the correct answer data. For example, in a case in which the image before biopsy is a mammographic image, the registration means 76 registers, as the correct answer data, the CC images of the left and right breasts and the MLO images of the left and right breasts in the mammographic image.

The learning data storage unit 77 is provided in an auxiliary storage device such as a hard disk or a solid state drive (SSD). Alternatively, the learning data storage unit 77 may be provided in a NAS connected to the network.

In addition, a correct answer data label is attached to a lesion candidate region image and the lesion candidate region image is stored as learning data in the learning data storage unit 77. Alternatively, in a case in which the discriminator 79 determines an image indicating that a lesion is present, the correct answer data label is attached to the image before biopsy acquired by the image-before-biopsy acquisition means 72 and the image before biopsy is stored as the learning data.

The learning means 78 directs the discriminator 79 to relearn the correct answer data stored in the learning data storage unit 77. The image analysis process 73 detects a lesion candidate region using the discriminator 79 that has learned the correct answer data in advance. The image analysis process 73 directs the first discriminator 79 to relearn the correct answer data which is the result of the determination of whether the detected lesion candidate region is a lesion from the biopsy result or directs the second discriminator 79 to relearn the correct answer data which is the result of the determination of whether the image before biopsy is an image indicating that a lesion is present from the biopsy result. This configuration makes it possible to further improve the discrimination performance. It is preferable to direct the discriminator 79 to learn the correct answer data and to update the image analysis process 73 in a case in which a certain amount of learning data is accumulated.

Figure 7:
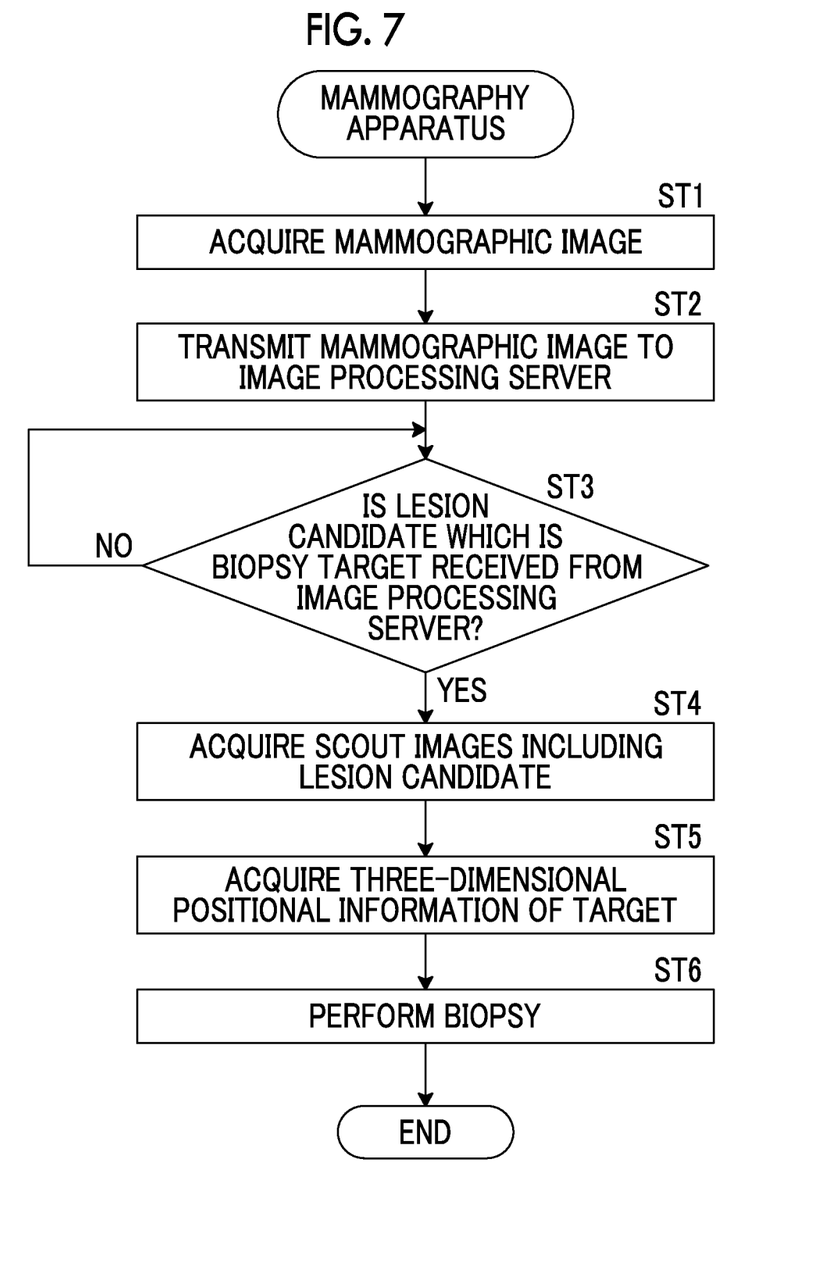
FIG. 7 is a flowchart illustrating an example of the flow of an imaging process of the mammography apparatus.
Figure 8:
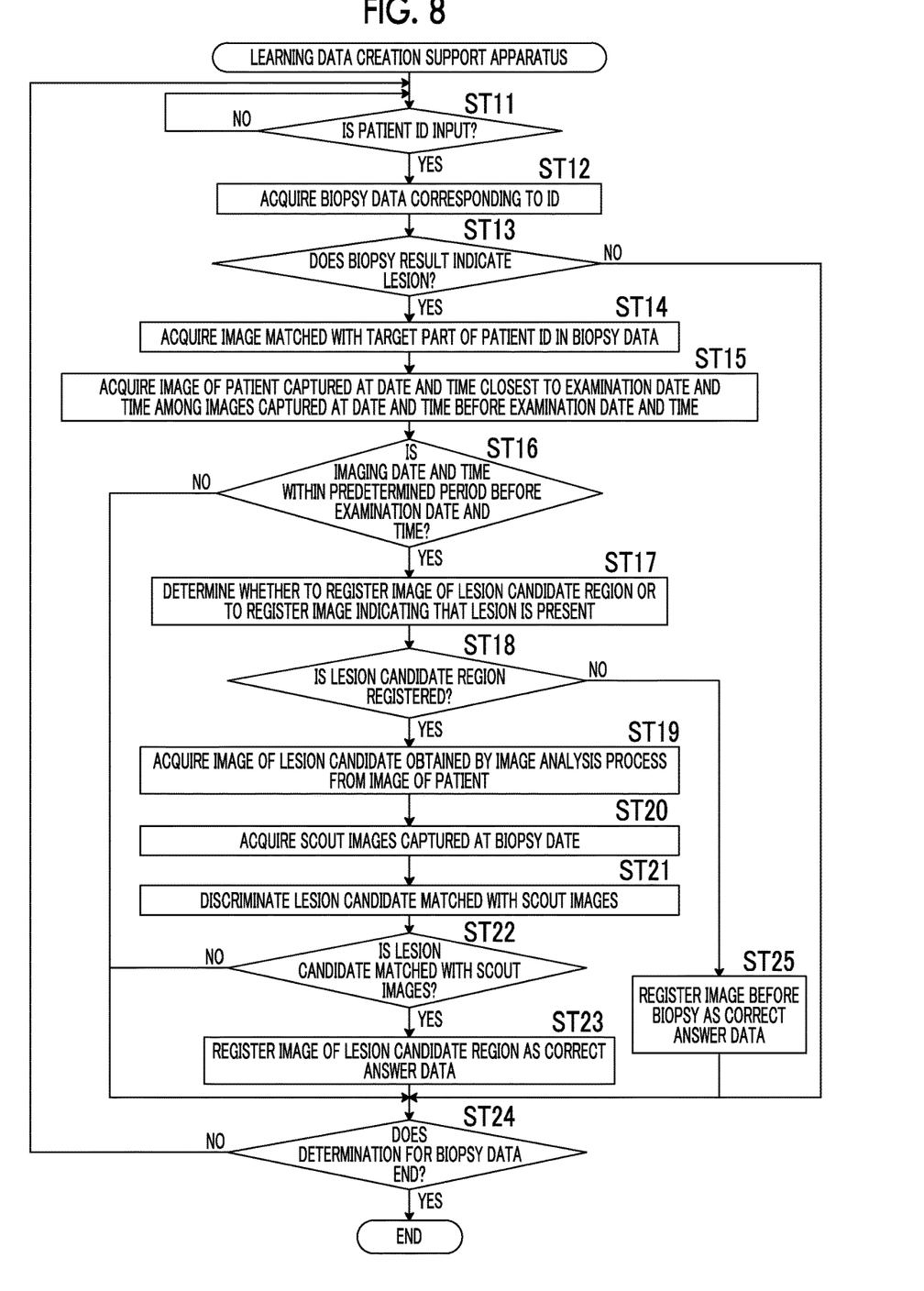
FIG. 8 is a flowchart illustrating an example of the flow of a learning data registration process.

Next, a method in which the mammography apparatus captures mammographic images and performs a biopsy and the image processing server creates learning data on the basis of the biopsy result will be described. FIG. 7 is a flowchart illustrating an example of the flow of an imaging process of the mammography apparatus. FIG. 8 is a flowchart illustrating an example of the flow of a learning data creation process of the image processing server (learning data creation support apparatus). The flow of a process from the capture of a mammographic image to the creation of learning data will be described according to the flowcharts illustrated in FIGS. 7 and 8.

First, the flow of the capture of an image will be described according to the flowchart illustrated in FIG. 7. The breast M of a patient is placed on the imaging table 14 of the mammography apparatus 2 in order to capture a mammographic image. The operator moves the arm 13 in the vertical direction with the operation unit 28 to adjust the height of the arm 13 according to the height of the breast M of the patient. In addition, the operator operates the operation unit 28 to direct the arm control unit 31 to incline the arm 13 according to whether to capture the images of the breast M in a mediolateral oblique (MLO) direction or a craniocaudal (CC) direction. In a case in which the operator positions the imaging table 14 at a height and an inclination angle suitable for imaging, the compression plate controller 34 compresses the breast until pressure against the compression plate 18 reaches a predetermined value. In addition, after the operator inputs various imaging conditions to the mammography apparatus 2, a command to start imaging is input. The radiation emitting unit 17 emits radiation according to the imaging conditions and the flat panel detector 15 acquires a mammographic image (Step ST1). Accessory information based on the DICOM standard is given to the acquired mammographic image and the mammographic image is transmitted to the image database 5. In addition, the mammographic image is transmitted to the image processing server 7 (Step ST2) and the image processing server 7 performs the image analysis process 73. The mammography apparatus 2 temporarily ends the capture of the images of the breast M and the determination result in Step ST3 is "NO" until a lesion candidate which is a biopsy target is received from the image processing server.

In the image processing server 7, the image analysis process 73 is performed for the mammographic image to detect lesion candidate regions such as a tumor and calcification. The detected lesion candidate regions and the positional information thereof are transmitted as the analysis results from the image processing server 7 to the radiologist WS 3. In the radiologist WS 3, marks are put on the lesion candidate regions of the mammographic image on the basis of the received analysis results and the lesion candidate regions are displayed. The radiologist interprets the mammographic image. In a case in which the radiologist designates a lesion candidate region requiring a biopsy among a plurality of lesion candidate regions displayed on the display with, for example, a mouse, the positional information of the designated lesion candidate region is transmitted from the radiologist WS 3 to the image processing server 7. For example, in a case in which a lesion candidate region is present in the inner upper part of the right breast, positional information indicating the inner upper part of the right breast is transmitted from the radiologist WS 3 to the image processing server 7. In addition, the image processing server 7 transmits the positional information of the lesion candidate region which is a biopsy target T to the mammography apparatus 2.

Then, in a case in which the mammography apparatus 2 receives the positional information of the lesion candidate region from the image processing server 7, the determination result in Step ST3 is "YES". In a case in which the breast M of the same patient is placed on the imaging table 14 in the same procedure as described above in order to perform a biopsy using the mammography apparatus 2, the compression plate controller 34 compresses the breast of the patient with the compression plate 18. Before needling, for example, two scout images obtained by capturing the images of the inner upper part of the right breast in two directions so as to include the lesion candidate region of the breast M which is the biopsy target T on the basis of the positional information of the received lesion candidate region as illustrated in FIG. 5 are acquired (Step ST4). The mammography apparatus 2 acquires the three-dimensional positional information of the target T from the two scout images (Step ST5). The needle position controller 35 of the biopsy unit 26 moves the tip of the biopsy needle 21 to the position of the target T on the basis of the three-dimensional positional information and the biopsy needle unit 22 inserts the biopsy needle 21 into the breast (Step ST6).

The case in which the positional information for capturing the scout images is received from the image processing server 7 has been described above. However, the operator of the mammography apparatus 2 may check, for example, an interpretation report and manually input an imaging position to the mammography apparatus 2 such that the scout images are captured.

In addition, for example, a pathologist performs a pathology examination for the tissues obtained by biopsy and the pathology examination WS 8 makes a pathology examination report including biopsy data. The pathology examination report that has been made, a patient ID, a pathologist ID, a lesion name, the positional information of a lesion, and the doctor's opinion are registered in the pathology report database 9.

Next, the flow of a learning data creation process of the image processing server 7, that is, the learning data creation support apparatus 7 will be described according to a flowchart illustrated in FIG. 8. In this embodiment, a case in which, if the pathology examination WS 8 makes a pathology examination report, the patient ID is transmitted to the learning data creation support apparatus 7, a mammographic image and biopsy data are acquired using the patient ID, and learning data is created will be described. In this embodiment, a case in which the user selects whether to register the image of the lesion candidate region as the learning data or to register the image before biopsy as the learning data in advance will be described. First, a case in which the image of the lesion candidate region is set to be registered as the learning data will be described.

First, in a case in which the patient ID on which a pathology examination report has been made is received from the pathology examination WS 8, the determination result in Step ST11 is "YES". The biopsy data acquisition means 71 searches for the pathology examination report corresponding to the patient ID from the pathology report database 9 and acquires biopsy data from the pathology examination report (Step ST12). In a case in which the biopsy result indicated by the biopsy data is a lesion, the determination result in Step ST13 is "YES". The image-before-biopsy acquisition means 72 acquires the mammographic image obtained by capturing the image of the breast which is a biopsy target part of the patient ID from the image database 5 (Step ST14). It is highly possible that the same patient was subjected to the mammography examination a plurality of times in the past and a plurality of mammographic images were stored in the image database 5. However, since whether to perform a biopsy for the breast of the patient is determined on the basis of the mammographic image captured immediately before the biopsy, an image captured at the date and time which is before the examination date and time and is closest to the examination date and time is acquired from the mammographic images corresponding to the patient ID of the patient who has been subjected to a biopsy (Step ST15). However, the biopsy is not determined on the basis of, for example, the old images captured one year or more ago. Therefore, in a case in which the acquired mammographic image is within, for example, two months before the biopsy date and time, the determination result in Step ST16 is "YES".

On the other hand, in a case in which the acquired mammographic image is not within, for example, two months before the biopsy date and time, the determination result in Step ST16 is "NO". In this case, since it is difficult to find a mammographic image for the biopsy result, registration is not performed. Until the determination of whether there is correct answer data for all of the biopsy data ends, the determination result in Step ST22 is "NO" and the process returns to Step ST11. The learning data creation support apparatus 7 waits for the input of the next patient ID.

In a case in which the determination result in Step ST16 is "YES", it is determined whether to register the lesion candidate region or to register the image indicating that a lesion is present (Step ST17). In a case in which the image of the lesion candidate region is registered as the learning data, the determination result in Step ST18 is "YES" and the lesion candidate region obtained by performing the image analysis process 73 for the mammographic image closest to the examination date and time is acquired (Step ST19). In addition, the scout image acquisition means 74 acquires the scout images of the same patient ID captured on the biopsy date from the image database 5 (Step ST20). In a case in which a plurality of lesion candidate regions are detected from the mammographic image by the image analysis process 73, the correspondence position determination means 75 determines whether there is a shadow of a lesion candidate region matched with the shadow appearing in the scout image (Step ST21).

In a case in which a lesion candidate region matched with the scout image is found, the determination result in Step ST22 is "YES" and the registration means 76 registers the lesion candidate region as the correct answer data in the learning data storage unit 77 (Step ST23). On the other hand, in a case in which a lesion candidate region matched with the scout image is not found, the determination result in Step ST22 is "NO" and the correct answer data is not registered in the learning data storage unit 77. In addition, until the determination of whether there is correct answer data for all of the biopsy data ends, the determination result in Step ST24 is "NO" and the process returns to Step ST11. The learning data creation support apparatus 7 waits for the input of the next patient ID.

Then, in a case in which another patient ID is input, the determination result in Step ST11 is "YES" and the biopsy data acquisition means 71 searches for a pathology examination report corresponding to the patient ID from the pathology report database 9 and acquires biopsy data from the pathology examination report (Step ST12). However, in a case in which the biopsy result indicated by the biopsy data is not a lesion (the determination results in Step ST13 and Step ST24 are "NO"), the process returns to Step ST11. The learning data creation support apparatus 7 waits for the input of the next patient ID.

As described in detail above, in a case in which the biopsy result indicates a lesion, a shadow corresponding to the biopsy result is more likely to be a lesion, as compared to a case in which the biopsy result does not indicate a lesion. Therefore, the learning data creation support apparatus 7 searches for the image captured before a biopsy and registers a lesion candidate region detected from the searched image as the correct answer data. As a result, it is possible to generate learning data without a complicated operation.

The case in which a plurality of lesion candidate regions are detected from the mammographic image has been described above. However, in a case in which only one lesion candidate region has been detected, the learning data creation support apparatus 7 may not determine whether a shadow in the lesion candidate region is matched with the shadow appearing in the scout image. In a case in which the biopsy result indicates a lesion, the detected lesion candidate region may be registered as the correct answer data in the learning data storage unit 77.

Next, a case in which the image before biopsy is set to be registered as the learning data will be described. A process from Step ST11 to Step ST16 is performed in the same way as described above to find a mammographic image which is an image before biopsy for the biopsy result. Then, it is determined whether to register the lesion candidate region or to register the image indicating that a lesion is present (Step ST17). In a case in which the image indicating that a lesion is present is registered as the learning data, the determination result in Step ST18 is "NO" and the mammographic image which is the image before biopsy for the biopsy result is registered as the correct answer data in Step ST25. Then, the process proceeds to Step ST24. The process from Step ST11 to Step ST24 is repeated until the determination of whether there is correct answer data for all of the biopsy data ends.

Figure 9:
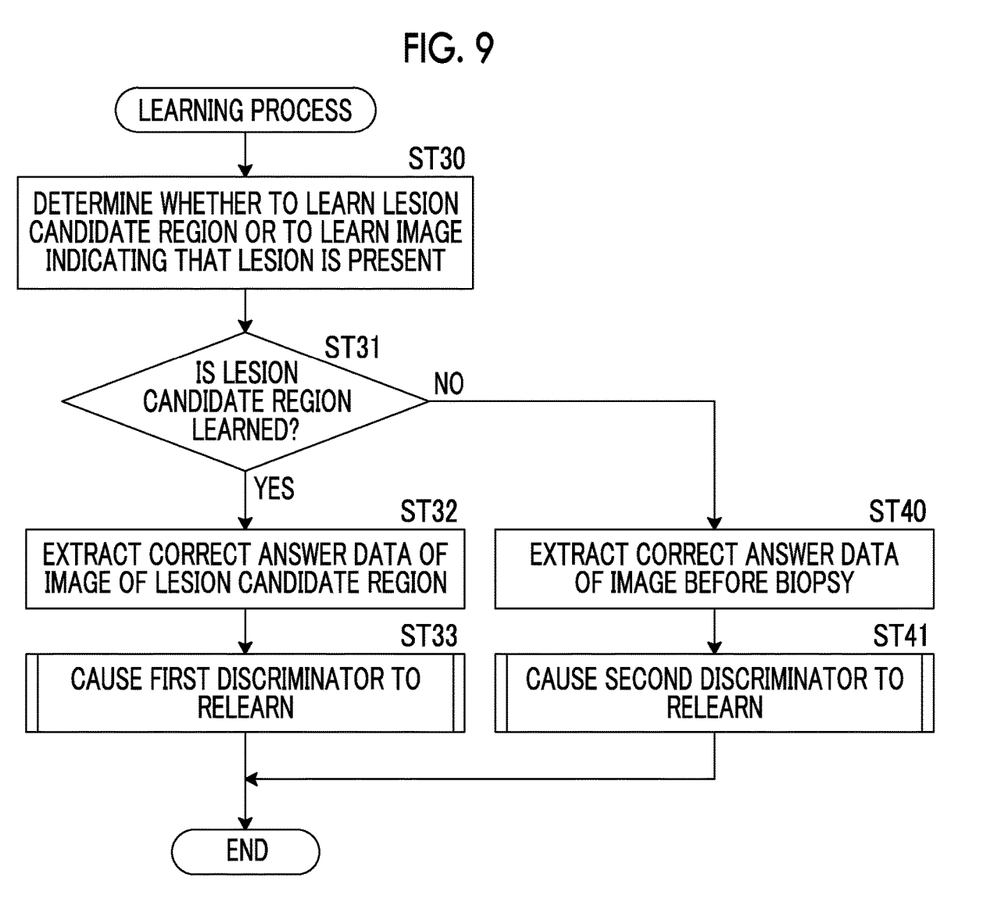
FIG. 9 is a flowchart illustrating an example of the flow of a process of causing a discriminator to learn.

Next, the flow of a process for causing the discriminator 79 of the image analysis process to learn the correct answer data accumulated in the learning data storage unit 77 will be described with reference to the flowchart of a learning process illustrated in FIG. 9.

In a case in which a certain amount of learning data is accumulated, the learning means 78 directs the discriminator 79 to perform relearning. First, it is determined whether to learn the lesion candidate region or to learn the image indicating that a lesion is present (Step ST30). In a case in which the lesion candidate region is learned, the determination result in Step ST31 is "YES" and the learning means 78 extracts the correct answer data of the image of the lesion candidate region from the learning data storage unit 77 (Step ST32) and directs the first discriminator 79 to perform relearning (Step ST33). The discriminator 79 that has performed relearning is incorporated into the image analysis process and the image analysis process is reinstalled in the image processing server 7.

On the other hand, in a case in which the image indicating that a lesion is present is learned, the determination result in Step ST31 is "NO" and the learning means 78 extracts the correct answer data of the mammographic image which is the image before biopsy from the learning data storage unit 77 (Step ST40) and directs the second discriminator 79 to perform relearning (Step ST41). The discriminator 79 that has performed relearning is incorporated into the image analysis process and the image analysis process is reinstalled in the image processing server 7.

As such, since the correct answer data created on the basis of the biopsy result is learned, it is possible to improve the discrimination performance of the image analysis process.

As described in detail above, since the discriminator performs relearning, it is possible to improve the discrimination performance of the image analysis process and to repeat the creation of learning data using the result of the image analysis process and the biopsy result. Since the learning data is created in this way, it is possible to continuously improve the performance of the image analysis process.

The case in which the correct answer data is created has been described above. However, the region in which the biopsy result is a lesion and the result of the image analysis process is determined to be a normal shadow may be registered as the incorrect answer data in the learning data storage unit 77 and the discriminator may learn both the correct answer data and the incorrect answer data.

The breast has been described above as an example. The invention may be applied to other organs (for example, the stomach, the intestines, the liver, the kidney, or the lungs) and the correct answer data or the incorrect answer data may be created according to the biopsy results of each organ.

In the above-described embodiment, the hardware structure of a processing unit that performs various processes of the learning data creation support apparatus is the following various processors. The various processors include a CPU which is a general-purpose processor that executes software (program) to function as various processing units, a programmable logic device (PLD) which is a processor whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process.

One processing unit may be formed by one of the various processors or may be formed by a combination of two or more processors of the same type or different types (for example, a combination of a plurality of FPGAs or a combination of a CPU and an FPGA). In addition, a plurality of processing units may be formed by one processor. A first example of the configuration in which the plurality of processing units are formed by one processor is an aspect in which one or more CPUs and software are combined to form one processor and the processor functions as a plurality of processing units. A representative example of the aspect is a computer such as a client apparatus or a server. A second example of the configuration is an aspect in which a processor that implements all of the functions of a system including the plurality of processing units with one integrated circuit (IC) chip is used. A representative example of the aspect is a system-on-chip (SoC). As such, the hardware structure of various processing units is formed by using one or more of the various processors.

EXPLANATION OF REFERENCES

1: medical information system
2: modality (mammography apparatus)
3: radiologist workstation
4: diagnosis and treatment department workstation
5: image database
6: interpretation report database
7: image processing server (learning data creation support apparatus)
8: pathology examination workstation
9: pathology report database
10: network
11: base
12: axis
13: arm
14: imaging table
15: flat panel detector
16: radiation accommodation unit
17: radiation emitting unit
18: compression plate
19: moving mechanism
20: support unit
21: biopsy needle
22: biopsy needle unit
24: moving mechanism
25: opening portion
26: biopsy unit
28: operation unit
31: arm control unit
34: compression plate controller
35: needle position controller
71: biopsy data acquisition means
72: image-before-biopsy acquisition means
73: image analysis process
74: scout image acquisition means
75: correspondence position determination means
76: registration means
77: learning data storage unit
78: learning means
79: discriminator
M: breast
P1, P2: irradiation position
T: target
Img1, Img2: scout image
z: distance

What is claimed is:

1. A learning data creation support apparatus comprising:
a database that stores plurality of images and reports of a patient;
a processor configured to
search the database and acquire biopsy data included in a report indicating a result of a biopsy performed for the patient;
search the database and acquire, as an image before biopsy, an image of a biopsy target part of the patient captured at a date and time within a predetermined range before an examination date and time of the biopsy;
determine that the biopsy result indicated by the biopsy data indicates a lesion;
perform an image analysis process on the image before biopsy to obtain an image of a lesion candidate region using a discriminator;
register as corrected answer data, based on the determination that the biopsy result indicates the lesion, the image of the lesion candidate region or the image before biopsy; and
update the discriminator by directing the discriminator to relearn the registered corrected answer data,
wherein, in a case a plurality of the lesion candidate regions are obtained by the image analysis, the processor is further configured to acquire at least one specific lesion candidate region corresponding to a position where the biopsy was performed, and to register at least one image of the specific lesion candidate region as correct answer data.

2. The learning data creation support apparatus according to claim 1,
wherein, in a case in which the image of the lesion candidate region is registered, the processor specifies a correspondence position corresponding to a position where the biopsy has been performed in the image before biopsy from two partial images of the target part captured in different directions, and
in a case in which the biopsy result indicates a lesion, the processor registers, as the correct answer data, an image of a lesion candidate region at a position matched with the correspondence position among positions of a plurality of lesion candidate regions obtained from the image before biopsy.

3. The learning data creation support apparatus according to claim 1, the processor further configured to:
in a case in which the image of the lesion candidate region is registered, detect a lesion candidate region, using the discriminator that has learned the correct answer data of the image of the lesion candidate region, and directing the discriminator to relearn the correct answer data of the registered image of the lesion candidate region.

4. The learning data creation support apparatus according to claim 1, the processor further configured to:

in a case in which the image before biopsy is registered, detect whether an image indicating a lesion is present, using the discriminator that has learned the correct answer data of the image before biopsy, and direct the discriminator to relearn the correct answer data of the registered image before biopsy.

5. The learning data creation support apparatus according to claim 1,
wherein the image of the biopsy target part is a mammographic image.

6. The learning data creation support apparatus according to claim 2, the processor further configured to:
in a case in which the image of the lesion candidate region is registered, detect a lesion candidate region, using the discriminator that has learned the correct answer data of the image of the lesion candidate region, and directing the discriminator to relearn the correct answer data of the registered image of the lesion candidate region.

7. The learning data creation support apparatus according to claim 2, the processor further configured to:
in a case in which the image before biopsy is registered, detect whether an image indicating a lesion is present, using the discriminator that has learned the correct answer data of the image before biopsy, and direct the discriminator to relearn the correct answer data of the registered image before biopsy.

8. The learning data creation support apparatus according to claim 2,
wherein the image of the biopsy target part is a mammographic image.

9. The learning data creation support apparatus according to claim 3,
wherein the image of the biopsy target part is a mammographic image.

10. The learning data creation support apparatus according to claim 6,
wherein the image of the biopsy target part is a mammographic image.

11. A learning data creation support method performed in a learning data creation support apparatus, the method comprising:
searching a database that stores plurality of images and reports of a patient and acquiring biopsy data included in a report indicating a result of a biopsy performed for the patient;
searching the database and acquiring, as an image before biopsy, an image of a biopsy target part of the patient captured at a date and time within a predetermined range before an examination date and time of the biopsy;
determining that the biopsy result indicated by the biopsy data indicates a lesion;
performing an image analysis process on the image before biopsy to obtain an image of a lesion candidate region using a discriminator;
registering as corrected answer data, based on the determination that the biopsy result indicates the lesion, the image of the lesion candidate region or the image before biopsy; and
updating the discriminator by directing the discriminator to relearn the registered corrected answer data,
wherein, in a case a plurality of the lesion candidate regions are obtained by the image analysis, acquiring at least one specific lesion candidate region corresponding to a position where the biopsy was performed, and registering at least one image of the specific lesion candidate region as correct answer data.

12. A non-transitory computer recording medium storing a learning data creation support program that performs the learning data creation support method performed in the learning data creation support apparatus according to claim 11 and causes a computer to perform:
searching a database that stores a plurality of images and reports of a patient and acquiring biopsy data including in a report indicating a result of a biopsy performed for the patient;
searching the database and acquiring, as an image before biopsy, an image of a biopsy target part of the patient captured at a date and time within a predetermined range before an examination date and time of the biopsy;
determining that the biopsy result indicated by the biopsy data indicates a lesion;
performing an image analysis process on the image before biopsy to obtain an image of a lesion candidate region using a discriminator; and
registering as corrected answer data, based on the determination that the biopsy result indicates the lesion, the image of the lesion candidate region or the image before biopsy; and
updating the discriminator by directing the discriminator to relearn the registered corrected answer data,
wherein, in a case a plurality of the lesion candidate regions are obtained by the image analysis, acquiring at least one specific lesion candidate region corresponding to a position where the biopsy was performed, and registering at least one image of the specific lesion candidate region as correct answer data.

* * * * *